United States Patent

Aufrichtig et al.

[11] Patent Number: 5,841,835
[45] Date of Patent: Nov. 24, 1998

[54] APPARATUS AND METHOD FOR AUTOMATIC MONITORING AND ASSESSMENT OF IMAGE QUALITY IN X-RAY SYSTEMS

[75] Inventors: Richard Aufrichtig, Wauwatosa; Alexander Y. Tokman, Waukeshe, both of Wis.

[73] Assignee: General Electric Company, Milwaukee, Wis.

[21] Appl. No.: 823,037

[22] Filed: Mar. 31, 1997

[51] Int. Cl.⁶ .................................................. G01D 18/00
[52] U.S. Cl. ............................................ 378/207; 378/204
[58] Field of Search .................................. 378/207, 204, 378/18, 58, 162, 163, 165

[56] References Cited

U.S. PATENT DOCUMENTS 5,276,726  1/1994  Galkin ...................................... 378/207
5,420,441  5/1995  Newman et al. ..................... 378/207 X
5,539,799  7/1996  Schulze-Ganzlin et al. ........... 378/207
5,544,238  8/1996  Galkin ..................................... 378/207

*Primary Examiner*—David P. Porta
*Attorney, Agent, or Firm*—B. Joan Haushalter; John H. Pilarski

[57] ABSTRACT

An image quality test phantom tool is provided for use in the calibration and standardization of digital x-ray fluoroscopy and radiography systems. A composite phantom has a base for providing mechanical stability, a mesh with a central cut-out overlaid on the base, inserts positioned in the cut-out, and a carrier for housing the composite phantom. A digital image of the phantom is processed to compute x-ray system image quality measurements.

7 Claims, 5 Drawing Sheets

APPARATUS AND METHOD FOR AUTOMATIC MONITORING AND ASSESSMENT OF IMAGE QUALITY IN X-RAY SYSTEMS

TECHNICAL FIELD

The present invention relates to measurement and verification of x-ray system parameters and, more particularly, to an image quality test device for automatic monitoring and assessment of image quality in digital x-ray fluoroscopy and radiography systems.

BACKGROUND ART

X-ray systems have long been used for imaging and measurement of anatomical structures. On conventional radiographs, the imaging receptor consists of film which is mounted in contact with intensifying screens which are thin sheets of fluorescent material. This screen-film combination is typically housed in a cassette. When the x-rays penetrate the object/patient being imaged, the x-ray energy is absorbed by the intensifying screen material, and a portion is converted into light. The light then exposes the film, hereby creating the image.

Soon after the discovery of x-ray, the fluoroscopic procedure in which an instantaneous and continuous image is displayed on a fluorescent screen was developed. In recent years, this technology has improved significantly. The first step was the introduction of the image intensifier tube which converts the x-ray image into a light image that can be visualized by the human eye. The next step was the introduction of a television camera system to transfer the output of the image intensifier to a larger television monitor. Finally, we have seen the development of digital fluoroscopy systems, on which the output of the television camera is digitized, and digitally enhanced using advanced image processing methods, prior to display on the monitor. The introduction of both the image intensifier tube and the television system has placed high requirements on a correct calibration of the entire x-ray systems image chain.

X-ray phantoms are known calibration devices and teaching aids for conventional and digital x-ray systems. Two general types of phantoms are available today, including (1) plastic replicas of the human body or specific portions thereof or actual human bones cast in plastic, and (2) physics-based phantoms which measure a particular response of the x-ray system. The first type is primarily used to train x-ray technicians in the proper positioning of the human body for the various x-ray images that are taken for diagnosis. The second class of phantoms is utilized during calibration and assessment of image quality of the x-ray system.

Extensive scientific work has been done in measuring x-ray dose and image quality of x-ray imaging equipment. Test phantoms and measurements have evolved to facilitate evaluation of an x-ray imaging machine. From a regulatory point of view, radiation dose is often the key parameter of concern. Today, the general policy is to protect patients from unreasonable radiation dose, while still allowing the radiologist to obtain an image of acceptable quality.

In recent years, there has been increased interest in independent, third party monitoring of image quality along with radiation dose. A variety of phantoms and dosimeters have been used for this type of application, and while dose tests are quantitative, the image quality tests are, for the most part, qualitative. Furthermore, existing image quality tests consist of highly iterative methods of calibration which utilize several different phantoms combined with many subjective visual evaluations. These systems, also, requires extensive user interaction.

Some disadvantages are inherent in existing approaches. One, there is always a cost associated with requiring technicians and/or scientists to interact with the system. Two, human interaction necessarily includes the risk of false readings.

With ever-increasing concern for the quality of care, there is increased interest in regulatory evaluation of x-ray equipment. However, this runs counter to the pressure on governmental agencies to reduce costs. Thus, a genuine need exists in the art for facilitating gathering of reliable, non-falsifiable image quality information.

SUMMARY OF THE INVENTION

The present invention provides an image quality test phantom (hardware and software) and methodology for automatic monitoring and assessment of image quality in digital x-ray fluoroscopy and radiography systems. Instead of using highly iterative methods of calibration and image quality verification which utilize many different phantoms combined with multiple subjective visual evaluations, the phantom according to the present invention provides an efficient and robust method for fast and objective image quality measurements and assessments.

In accordance with one aspect of the present invention, an x-ray image quality test tool comprises two parts, a hardware portion, specifically a composite phantom, and a software portion. The composite phantom comprises a copper sheet with an overlaid steel mesh. A central part of the mesh is cut out, and inserts comprising a resolution pattern, a contrast-detail phantom, a step wedge phantom and a line phantom are positioned in the center overlaying the copper sheet. The composite phantom is mounted in a housing, or carrier, which attaches to the front of the x-ray system imager. The software comprises various image and signal processing algorithms which, when applied to the digital image of the phantom, provide all necessary logic to compute the required x-ray system image quality measures.

Accordingly, it is an object of the present invention to provide an image quality test tool, comprised of a composite phantom and associated software, for automatic monitoring and assessment of image quality, which is particularly well suited for use with digital x-ray fluoroscopy and radiography systems. It is a further object of the present invention to provide a method for using the phantom to trend and calibrate such systems.

Other objects and advantages of the invention will be apparent from the following description, the accompanying drawings and the appended claims.

DETAILED DESCRIPTION OF THE PREFERRED EMBODIMENTS

The present invention proposes an x-ray image quality test phantom which provides an efficient method for very fast and objective image quality measurements and assessments. A significant aspect of the present invention is that it provides the capability of measuring critical x-ray system image quality parameters objectively and instantaneously.

Figure 1A:
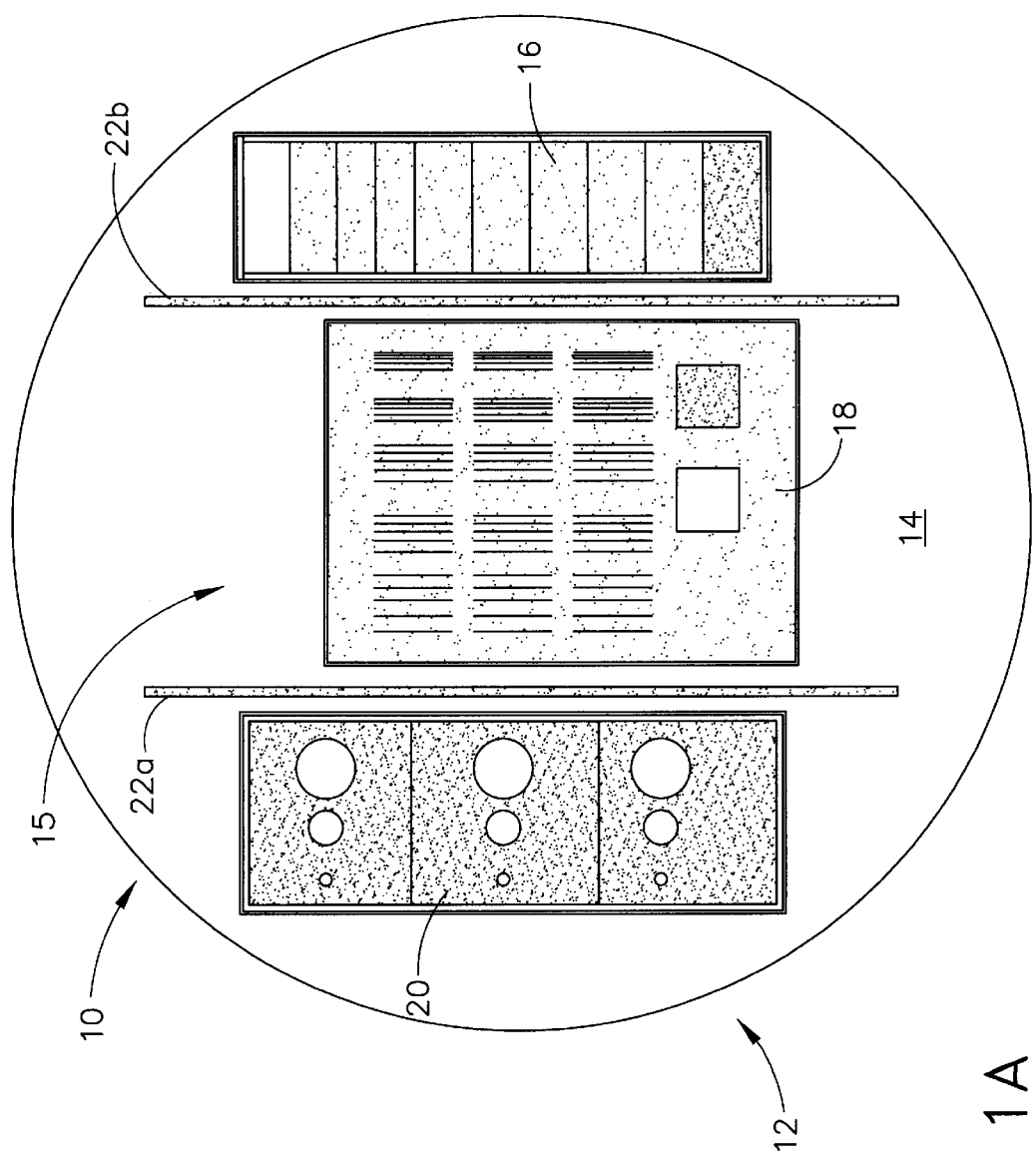
FIGS. 1A and 1B are a top view and a cross-sectional view, respectively, of the image quality test phantom, in accordance with the present invention.
Figure 1B:
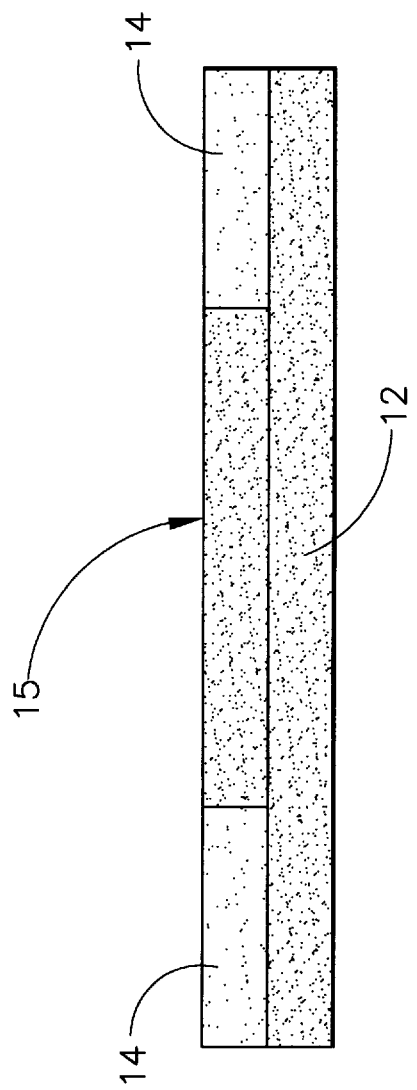

Referring now to the drawings, in FIGS. 1A and 1B there is illustrated an image quality test phantom 10, in accordance with the present invention. Copper sheet 12, generally circular, serves as a base for the composite phantom. The purpose of the copper sheet is to provide the mechanical stability for the phantom, an appropriate x-ray beam quality for the image analysis and an appropriate dynamic range. A steel mesh 14 is placed on top of the copper sheet 12. A central, approximate square portion, of the mesh is cut out. The remaining part of the steel mesh is used in the computation of resolution uniformity of the x-ray image.

In the center of the mesh-free region the composite phantom comprises an insert 15, containing a ten level copper step wedge 16, a resolution pattern 18, a contrast detail phantom 20, and lead line phantoms 22. The size of the step wedge 16 is approximately 2.5 cm×5.5 cm with steps ranging from 0.254 mm to 2.54 mm. The purpose of the step wedge is to access the dynamic range and linearity of the x-ray system.

The resolution pattern 18 covers spatial frequencies from 0.5 line-pairs/mm (1p/mm) to 5 1p/mm created from 0.1 mm lead foil. It also includes three 1 cm×1 cm regions with 0 mm, 0.1 mm and 1.0 mm lead. The resolution pattern is used in the computation of x-ray system modulation transfer function with the square regions used for normalization purposes.

An aluminum contrast-detail phantom 20 comprises three steps with three apertures on each step. The diameters of the three apertures are, for example, 7.6 mm, 3.8 mm, and 1.9 mm, and the respective thicknesses of the steps can be defined as 1 mm, 2 mm and 3 mm. The purpose of the contrast-detail phantom is to assess the relative contrast and contrast-to-noise ratio of the x-ray system. The aluminum base provides the appropriate contrast levels and form factor. Lead line phantoms 22a, 22b, located on the outer edges of the resolution phantom, are used for distortion measurements.

Figure 2:
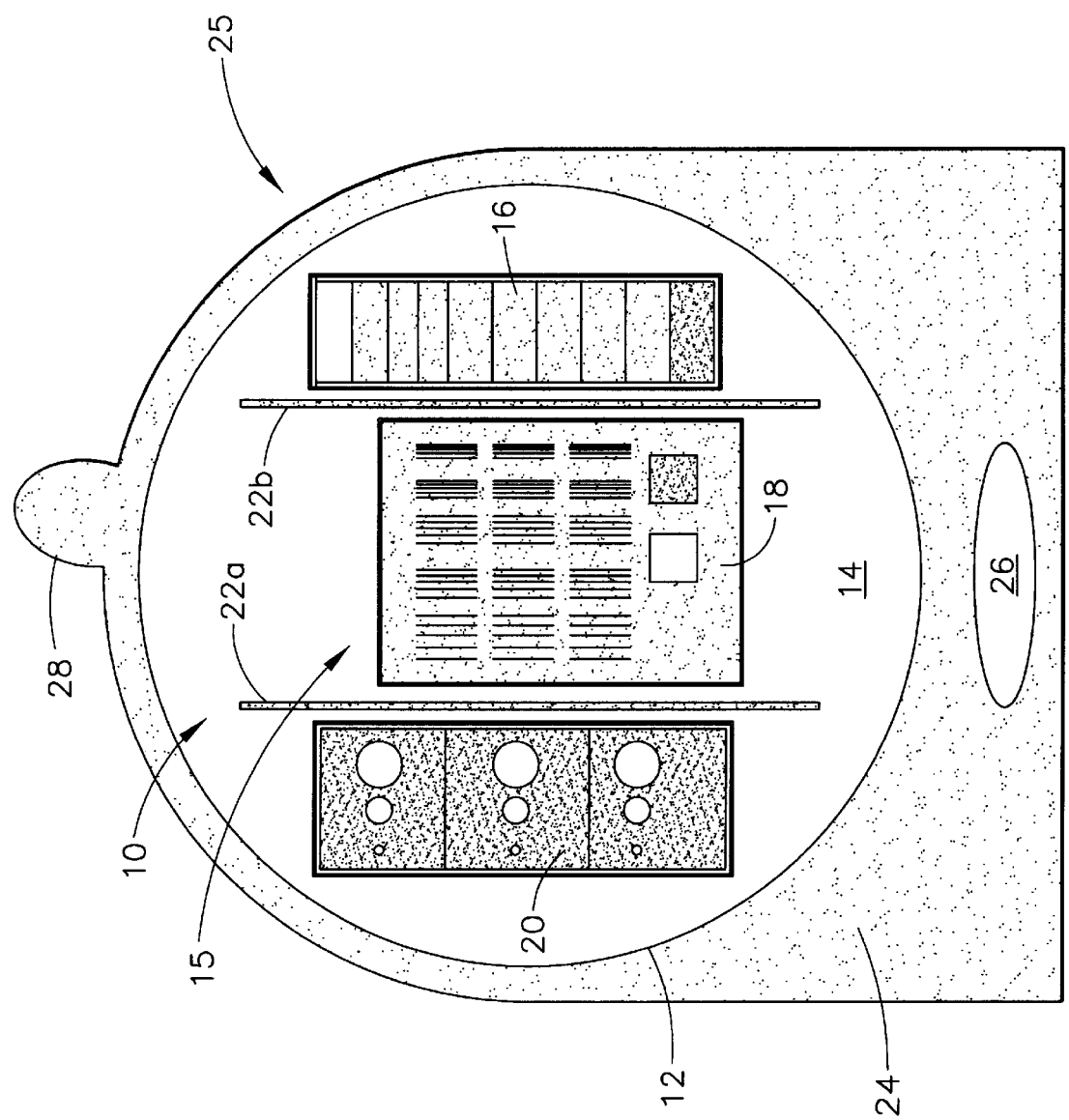
FIG. 2 illustrates an example of the image quality test phantom positioned in its housing (carrier) for mounting in front of an image intensifier based x-ray system.
Figure 3:
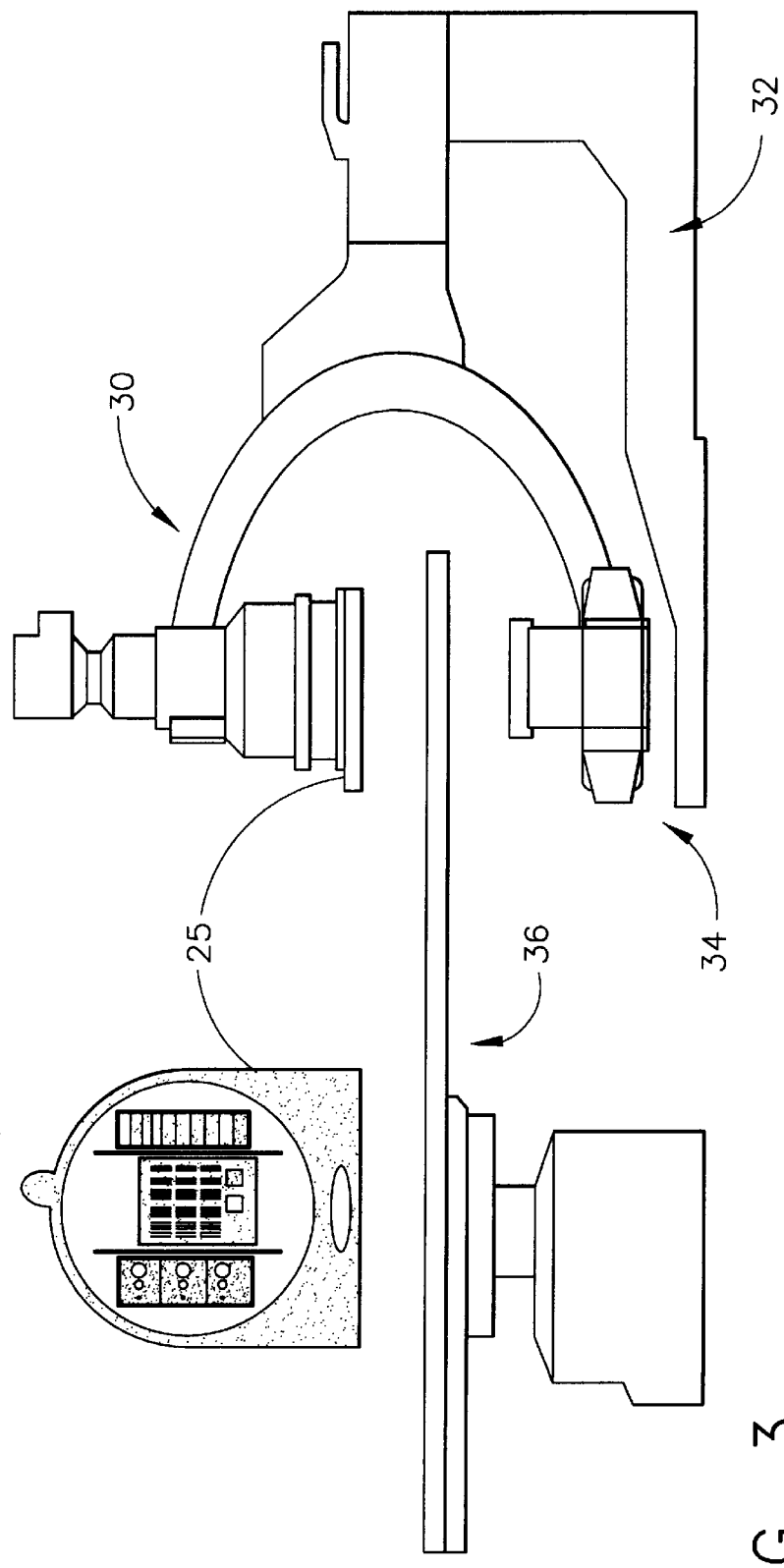
FIG. 3 illustrates an example of the image quality test phantom with its housing, placed on a vascular x-ray system.

An example of the image quality phantom 10 mounted in a carrier 24 is shown in FIG. 2. The carrier 24 can include a handle 26 and an alignment pin 28. The actual application of the image quality phantom 10 with the carrier 24, comprising a composite 25, to a vascular x-ray system (with removable grid), is shown in FIG. 3. For other systems, the composite 25 can be sized to attach to the front face of image intensifier 30 or other digital imager. As illustrated in FIG. 3, the image quality phantom composite 25, comprising the phantom 10 and the carrier 24, is mounted in front of the image intensifier 30. An x-ray positioner 32 positions the image intensifier 30 and x-ray tube 34, above and below x-ray table 36, respectively.

Once the phantom 10 has been arranged, a methodology for automatic monitoring and assessment of image quality in the digital x-ray system is provided, in accordance with the present invention. The second integral part of the image quality tool of the present invention, then, is the software functionality. The present invention provides software methodology for complete image quality assessment process automation, in conjunction with the test phantom hardware.

Once a digital x-ray image of the phantom 10 is acquired, it can then be processed in accordance with the present invention.

Figure 4:
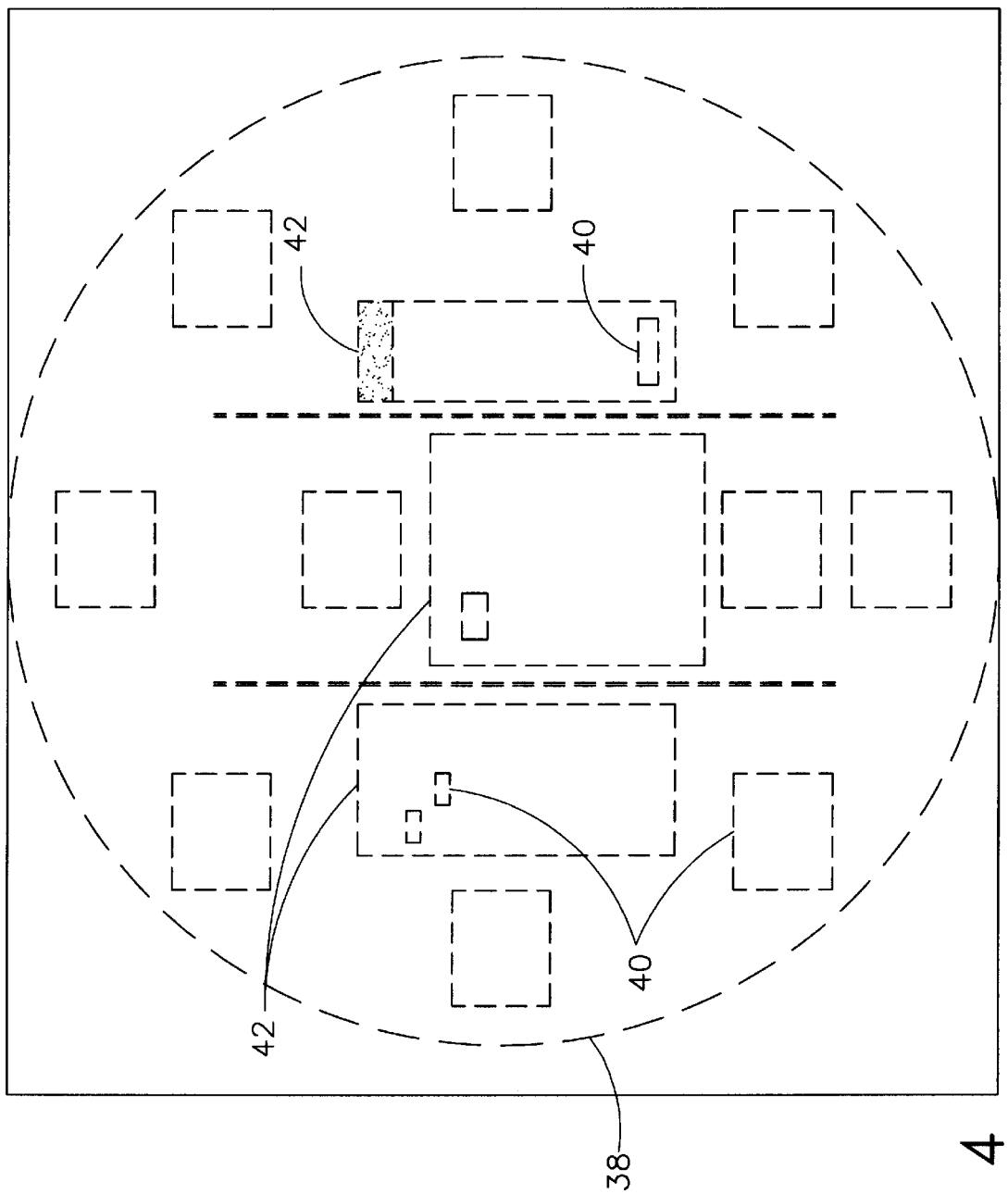
FIG. 4 illustrates an example of an actual phantom-based digital image together with overlayed regions of interest automatically identified and determined by imaging software, in accordance with the present invention.

First, an initial localization of the resolution 18, step wedge 16, contrast-detail 20 and lead wire 22a and 22b phantoms is done by calculating spatial derivatives through cross-sections of the image. Localized filtration with an N×N edge enhancement kernels are performed in areas around the initial estimates. Additional localization information is obtained by tracking circular edge 38 of the image, as illustrated in FIG. 4. An edge linking algorithm, such as obtained by dynamic programming, is performed to precisely specify the locations of the resolution 18, step wedge 16, contrast detail 20 and lead wire 22a and 22b phantom edges, where the edges are referenced as 42. A second order polynomial warping is performed to automatically predict the location of regions of interest on the image, based upon the known geometry of the image quality phantom 10. The desired location of the regions of interest are at the specified frequencies and normalization points on the resolution phantom 18, at each level of the step wedge 16, at each disk and surrounding area of the contrast-detail phantom 20, and in multiple (such as, by way of example, eight) peripheral and two central areas of the mesh pattern 14. First and second order statistics and their variates are calculated at each region of interest, to estimate the system resolution, uniformity, dynamic range, contrast-to-noise, and noise. System distortion is estimated from polynomial fitting of the edge tracking data from the two lead wires 22a and 22b.

Referring to FIG. 4, there is illustrated an example of the actual digital image of the composite phantom. Overlay figures represent the critical image areas used in the assessment of the x-ray system image quality. All regions were identified and isolated by the automatic software without any user interaction. If an additional digital image of a flat copper sheet is available, a digital subtraction of the flat field image from the image quality phantom 10 image is performed to remove bias introduced by system brightness non-uniformities. The subtraction image is then used in the resolution 18, step wedge 16 and contrast-to-noise calculations.

Since the detection of phantoms, the positioning of boxes, i.e., regions of interest 40, examples of which are shown in FIG. 4, and the computations of parameters are all accomplished automatically, in accordance with the present invention, the approach of the present invention is particularly suitable for use in automatic trending, calibration and optimization of parameters within the x-ray imaging chain.

For trending purposes, the phantom can be imaged at specified intervals, for example, every two weeks, and the resulting data can be recorded and compared to an established data base. The results can be made available to an off-site service center, to allow for remote analysis and assessment.

With respect to system optimization, the phantom provides data needed for automatic closed-loop calibration. Since most adjustments on a modern fluoroscopy system are software controlled, iterative methods, such as least squares, can be used to optimize the system parameters that are measured by the phantom. One process of automatic calibration, in accordance with the present invention, measures the initial system with the image quality phantom 10. If the measured value is out of specification, a software controlled adjustment is performed on the system. The new state is then remeasured with the image quality phantom 10, and an iterative method such as a least squares iterative optimization is used to minimize the difference between the measured value obtained by system adjustments and the engineering specifications.

The present invention provides for processing of a digital image, analysis of image quality, and assessment of x-ray system image quality. A digital subtraction of a flat field image can be performed from the image quality phantom image to remove bias introduced by system brightness non-uniformities. The subtraction image can then be used in resolution, step wedge and contrast-to-noise calculations.

Analysis of image quality of the x-ray system includes automatically providing trending image quality data. The trending can be performed by the phantom and can be imaged at specified intervals, for example, every two weeks, and the resulting data can be recorded and compared to an is established data base. Assessment of x-ray system image quality can further include remote monitoring of such systems via an off-site service center.

In accordance with the present invention, a first composite x-ray image quality phantom is used to effectively and objectively measure image system parameters such as resolution, uniformity, dynamic range, contrast-to-noise, distortion and noise. The present invention further proposes a method of use of the phantom to automatically, without any user interaction, detect the location of individual components in a digital x-ray image of the composite image quality phantom. This involves the use of edge detection and tracking, and polynomial warping to estimate the location of regions of interest within the image quality phantom. The present invention provides for the use of the image quality phantom in system image quality trending, both local and remote, and as data feedback of a closed loop design that uses an iterative method to optimize system performance.

The invention has been described in detail with particular reference to certain preferred embodiments thereof, but it will be understood that modifications and variations can be effected within the spirit and scope of the invention.

What is claimed is:

1. A method for processing a digital x-ray image to automatically assess image quality of a system, comprising the steps of:

providing a digital image of a composite phantom, including images of inserts including a resolution pattern, a contrast detail phantom, a multiple level copper step wedge, and lead wire phantoms; and applying processing means to the digital image for computing x-ray system image quality measurements, wherein the step of applying processing means includes calculating derivatives through cross-sections of the digital image to provide initial localization of the resolution pattern, step wedge, contrast detail phantom and lead wire phantoms;

providing localized filtration with N×N edge enhancement kernels in areas around initial estimates;

precisely specifying locations of the resolution, step wedge, contrast-detail phantom, and lead wire phantoms;

tracking a circular edge of the image to obtain additional localization information;

performing a second order polynomial warping to automatically predict location of regions of interest on the image;

calculating first and second order statistics and their variates at each region of interest to estimate system resolution, uniformity, dynamic range, contrast-to-noise, and noise; and estimating system distortion from polynomial fitting of the edge tracking data from the two lead wire phantoms.

2. A method for processing a digital x-ray image as claimed in claim 1 further comprising the step of performing a digital subtraction of a flat field image from the digital x-ray image of the phantom to remove bias introduced by system brightness non-uniformities and to generate a subtraction image.

3. A method for processing a digital x-ray image as claimed in claim 2 further comprising the step of using the subtraction image in resolution, step wedge and contrast-to-noise calculations.

4. A method for processing a digital x-ray image as claimed in claim 1 further comprising the step of analyzing image quality of the x-ray system by automatically providing trending image quality data.

5. A method for processing a digital x-ray image as claimed in claim 4 wherein the trending performed by the phantom is imaged at predetermined intervals.

6. A method for processing a digital x-ray image as claimed in 5 further comprising of the step of assessing x-ray system image quality by remotely monitoring trending data.

7. A method for processing a digital x-ray image as claimed in 4 further comprising of the step of calibrating image quality of the x-ray system.

* * * * *